United States Patent [19]

Hem et al.

[11] Patent Number: 4,970,079

[45] Date of Patent: Nov. 13, 1990

[54] METHOD AND COMPOSITION OF OXY-IRON COMPOUNDS FOR TREATMENT OF HYPERPHOSPHATEMIA

[75] Inventors: Stanley L. Hem, West Lafayette; Joseph L. White, Lafayette, both of Ind.

[73] Assignee: Purdue Reserach Foundation, West Lafayette, Ind.

[21] Appl. No.: 361,494

[22] Filed: Jun. 5, 1989

[51] Int. Cl.$^5$ ................................ A61K 33/26
[52] U.S. Cl. .................... 424/646; 424/647; 424/648
[58] Field of Search ................ 424/647, 648, 646

[56] References Cited

U.S. PATENT DOCUMENTS

| | | | |
|---|---|---|---|
| 4,181,718 | 1/1980 | Mason et al. | 424/180 |
| 4,474,853 | 10/1980 | Watanabe | 428/403 |
| 4,581,141 | 5/1983 | Ash | 210/502 |
| 4,668,400 | 5/1987 | Veech | 210/647 |
| 4,870,105 | 10/1989 | Fordtran | 514/557 |

OTHER PUBLICATIONS

Mann et al., Formation of Iron Oxides in Unilamellar Vessicles. J. Colloidal Interface Sci. 122(2) 326–335 (1988).

Coburn, Jack W., M.D. and Isidro B. Salusky, M.D., "Control of Serum Phosphorus in Uremia", *The New England Journal of Medicine*, Apr. 27, 1989, pp. 1140–1142.

Stucki, J. W., B. A. Goodman and U. Schwertmann, "Iron in Soils and Clay Minerals", Published in cooperation with NATO Scientific Affairs Division.

*Primary Examiner*—Douglas W. Robinson
*Assistant Examiner*—Gary E. Hollinden
*Attorney, Agent, or Firm*—Barnes & Thornburg

[57] ABSTRACT

Oxy-iron compounds are useful for the treatment and prevention of hyperphosphatemia. Such compounds, particularly those exhibiting high surface area, can be administered orally to bind and inhibit absorption of dietary phosphate, or such compounds can be contacted with the dialysate in a hemodialysis unit to enhance reduction of serum phosphate of patients undergoing hemodialysis.

20 Claims, No Drawings

METHOD AND COMPOSITION OF OXY-IRON COMPOUNDS FOR TREATMENT OF HYPERPHOSPHATEMIA

FIELD OF INVENTION

This invention relates to the control of serum phosphate. More particularly, this invention is directed to a method for treatment and prevention of hyperphosphatemia in patients suffering that condition or predisposed to development of that condition.

BACKGROUND AND SUMMARY OF THE INVENTION

Hyperphosphatemia in patients with chronic renal failure is a serious problem which may lead to osteoitis fibrosa or calcium phosphate deposition in soft tissue. Various approaches have been used to lower serum phosphate. Aluminum hydroxide in an oral dosage form has been used to bind dietary phosphate. However, aluminum accumulates in patients with renal failure and its accumulation has been associated with dysfunction of various organ systems. Aluminum-associated osteomalacia has been shown to occur in patients whose only substantial exposure to aluminum was their intake of aluminum-containing phosphate binders.

Calcium carbonate therapy is another method which has been used for serum phosphate control. Serum calcium levels are known to increase significantly after treatment with calcium carbonate, in spite of decreased mean calcitriol dosage and suppression of parathyroid activity. This increase in serum calcium is thought to be attributed to increased gastrointestinal absorption of calcium that is not vitamin D dependent. Calcification of soft tissues and the vasculature are a potential risk associated with elevated calcium/phosphate ion product. Metastatic calcifications of the eyes, joints, viscera, skin and arteries can occur as calcium phosphate salts precipitate as a direct consequence of supersaturation of body fluids with calcium phosphates. Hyperphosphatemia has been seen as the most important factor in the mechanism of soft-tissue calcification in uremia. Additionally, calcium carbonate is not suitable for use in chronic renal failure patients who are hypercalcemic. Gastrointestinal distress may be manifested in some patients taking calcium carbonate. A recent letter in the *New England Journal of Medicine* [Stein et al., Vol. 316, p. 109 (1987)] reported high serum values and pancolonic impaction in patients with end-stage renal disease in which calcium carbonate was substituted for aluminum binders. The writers there cautioned against overzealous use of calcium carbonate as a phosphate binder.

Magnesium-containing phosphate binders have been used for treatment of hyperphosphatemia. However, such binders have been associated with hypermagnesemia, even with the use of a low magnesium dialysate. Other products advocated for use as phosphate binders such as calcium and iron cation loaded polyuronic acids require dosages of 5–10 grams per day.

There is recognized in the medical community a significant need for the development of a phosphate binder which ideally should be palatable, free of even minor side effects, inexpensive and very efficient in binding phosphate under physiological conditions. Accordingly, it is one object of this invention to provide a method for controlling serum phosphate utilizing a phosphate binding oxy-iron compound.

It is another object of this invention to provide a composition in an oral dosage form for inhibiting the absorption of dietary phosphate.

It is still another object of this invention to provide a composition which not only has been identified as an efficient phosphate binder, but has the added advantage of being insoluble or but slightly soluble in physiological fluids.

Another object of this invention is to provide a method for enhancing reduction of a patient's serum phosphate levels during hemodialysis by contacting a phosphate binding oxy-iron compound with the dialysate.

In accordance with this invention oxy-iron compounds, including particularly iron oxides and iron oxyhydroxides, have been determined to be effective agents for preventing absorption of ingested phosphates in the digestive tract. Not only do such compositions exhibit a high adsorptive capacity for phosphate, but they also exhibit low solubility in physiological fluids, including gastric juices, thereby lessening the probability of side effects due to absorption of solubilized iron compounds. Oxy-iron compounds can be utilized in accordance with this invention in an oral dosage form to bind and thereby prevent absorption of ingested phosphate from the intestine and, alternatively, can be used as an additive in dialysate used for hemodialysis to effect and maintain a low phosphate concentration in the dialysate and thereby promote reduction of a patient's serum phosphate level during hemodialysis.

Synthetic ferrihydrite ($Fe_5O_7(OH) \cdot 4H_2O$), a preferred oxy-iron compound for use in accordance with the present invention has been found to exhibit a high adsorptive capacity for phosphate, 32 mg P/g and was virtually insoluble in simulated gastric acid. It is projected that a 174 mg dose of ferrihydrite can adsorb the same amount of phosphate as 10 ml of the art-recognized aluminum hydroxide phosphate binder.

DETAILED DESCRIPTION OF THE INVENTION

There is provided, in accordance with this invention, a method of controlling serum phosphate levels in patients suffering from hyperphosphatemia or patients predisposed to development of a hyperphosphatemic condition. Patients experiencing chronic or acute renal insufficiencies requiring dialysis are among those most prone to develop hyperphosphatemio conditions.

The method in accordance with this invention comprises contacting ingested phosphate with an oxy-iron compound selected from the group consisting of iron oxides, iron oxyhydroxides, and iron hydroxides. Therapeutic benefit can be realized in accordance with such method by administering an oxyacid compound orally to a patient to contact and bind with ingested phosphate in the patient's digestive tract, and thereby prevent its systemic absorption.

Alternatively, the oxy-iron compound can be utilized to contact phosphate in the dialysate of a hemodialysis (artificial kidney) unit wherein substances are removed from the blood by diffusion across a semi-permeable membrane into a second fluid (the dialysate). Hemodialysis systems are well known in the art. See, for example, that described in U.S. Pat. No. 4,581,141, issued Apr. 8, 1986, the disclosure of which is incorporated herein by reference. The addition of an oxy-iron compound to the dialysate lowers the concentration of phosphate dissolved in the dialysate and thereby enhances the concentration differential dependent migration of phosphate ions from the patient's blood across the intermediate semi-permeable membrane and into the dialysate. Whether the oxy-iron compound is brought into contact with ingested phosphate in the digestive tract of a patient or in a dialysate utilized for patient hemodialysis, the phosphate binding oxy-iron compound is effective to control (i.e., prevent the build-up) of phosphate ions in the patient's body fluids, while at the same time, due to their low solubility, provide little risk of side effects.

Oxy-iron compounds useful in accordance with the present invention include iron oxides, iron hydroxides, and iron oxyhydroxides. Many such compounds are known in the art. Suitable oxy-iron compounds include naturally occurring and synthetic forms of the following minerals: Hematite ($\alpha$-$Fe_2O_3$), Ilmenite ($FeTiO_3$), Magnetite ($Fe_3O_4$), Maghemite ($\gamma$-$Fe_2O_3$), Goethite ($\alpha$-FeOOH), Lepidocrocite ($\gamma$-FeOOH), Akaganeite ($\beta$-FeOOH), Ferrihydrite ($Fe_5O_7(OH) \bullet 4H_2O$), and Ferroxyhite ($\delta'$-FeOOH). Suitable oxy-iron compounds can be amorphous or crystalline and include, as well, iron oxides and iron oxyhydroxides that can be prepared by coprecipitation of iron with one or more other metal ions. It is preferred that oxy-iron compounds for use in accordance with the present invention have a surface area of at least 50 $m^2/g$ to about 500 $m^2/g$, more preferably at least about 200 $m^2/g$. Typically the higher the surface area, the more efficient the oxy-iron compound is as a phosphate binder. Preferred oxy-iron compounds for use in accordance with this invention, therefore, exhibit low solubility in gastric acids and physiological fluids, and high surface area/phosphate binding capacity. Synthetic ferrihydrite is most preferred because of its high surface area.

In a preferred embodiment of this invention, the oxy-iron compounds are formulated as a therapeutic dosage form for oral administration to a patient afflicted with hyperphosphatemia or predisposed to develop that condition. Thus, the oxy-iron compound can be formulated as a liquid or gel suspension, or in a unitary solid dosage form such as a compressed tablet or capsule. Methods and excipients for preparation of both gel and solid dosage forms are well known in the art. The oral dosage form should be formulated to contain sufficient oxy-iron compound to bind, upon ingestion by the patient, sufficient ingested phosphate in the patient's intestinal tract to inhibit the absorption of ingested phosphate and thereby reduce the probability of either the development of a hyperphosphatemic condition or the complication of an already existing hyperphosphatemic condition. Thus, each oral dose of the therapeutic oxy-iron containing composition in accordance with this invention can contain from about 50 mg to about 500 mg or more of oxy-iron compound. The amount of oxy-iron compound to be administered will depend on the severity of the patient's condition, the nature of the patient's diet and the surface area/phosphate binding capacity of the oxy-iron compound used in the formulation. The dosages of oxy-iron compounds to be administered in accordance with this invention can be increased, if necessary, to correspond to the level of phosphate binding required in the patient's digestive tract.

In an alternative embodiment of this invention, an oxy-iron compound can be contacted with the dialysate of a hemodialysis unit (an artificial kidney) to reduce the concentration of soluble phosphate in the dialysate. The reduced soluble phosphate concentration in the dialysate enhances diffusion of phosphate in the patient's blood across the semi-permeable membrane separating the blood and the dialysate in the hemodialysis unit. Thus, oxy-iron compounds added to or contacted with the dialysate function to enhance the reduction of a patient's serum phosphate levels during hemodialysis. The phosphate binding oxy-iron compound can be added to the dialysate, for example, to a dialysis slurry such as that described in U.S. Pat. No. 4,581,141, issued Apr. 8, 1986, or the dialysate can be contacted with the oxy-iron compound by circulation through a separate cartridge or chamber containing the oxy-iron compound in which soluble phosphate in the dialysate is bound by the contained oxy-iron compound.

Oxy-iron compounds utilized in accordance with the present invention exhibit low water solubility over a wide pH range. Thus, they contribute little to the levels of soluble iron concentration in either the digestive tract or in the dialysate of a hemodialysis unit. This offers a significant advantage for the use of the oxy-iron compounds in accordance with this invention over the aluminum and calcium-containing phosphate binders which have been used heretofore to treat and prevent hyperphosphatemia.

EXAMPLES

Methods and Materials

Two iron oxide minerals, goethite and ferrihydrite, were evaluated for potential phosphate binding properties. These minerals occur naturally in soils and can be easily synthesized. Goethite was prepared by pouring 900 ml of 1 M KOH into 100 ml of 1 N $Fe(NO_3)_3 \bullet 9\ H_2O$ contained in a 2-liter propylene bottle, then adding enough deionized water to make 2 liters of solution. The suspension was placed in a forced-draft oven at 70° C. for 14 days to crystallize goethite. The suspension was then adjusted to pH 7 using 1N HCl and dialyzed against deionized water for 4 days.

Ferrihydrite was synthesized by titrating 100 ml of 1 N $Fe(NO_3)_3 \bullet 9\ H_2O$ with 1 N KOH to a stable pH of 8 and then dialyzing the precipitate against deionized water for 4 days.

Total iron content was determined after dissolving 30 mg samples in 20–40 ml of concentrated HCl. Oxalate-soluble iron was determined by extracting 30 mg samples in 20 ml of pH 3 ammonium oxalate in the dark for 2 hours. Iron in the extracts was determined by atomic absorption spectroscopy; surface area was determined by ethylene glycol monoethyl ether absorption.

Adsorption studies were conducted at pH 7.5, 37° C. using radiolabeled P-32 to determine the phosphate binding capacity. For each phosphate binder, 5 test solutions were prepared having a final volume of 55 ml and containing either 500 mg goethite or 50 mg ferrihydrite along with a blank solution containing no phosphate binder. The phosphorus concentrations in the test solutions were 0.03139, 0.1405, 0.2992, 0.5011, and 0.7677 mg P/ml. The phosphorus concentration of the blank was 0.5011 mg P/ml. Each solution, including the blank, also contained approximately 2.2 $\mu$Ci P-32. Following a 3-hour absorption period in a 37° C. shaker/water bath and centrifugation at 5400 rpm for 25 minutes, the activity of 1 ml of clear supernatant from each sample and the blank was determined using a liquid scintillation counter with external standardization. The activity value of the blank was subtracted from the activity of the test solution to correct for radioactive decay and self-absorption. These values were then used to calculate the adsorptive parameters of goethite and ferrihydrite.

The fraction of the dose expected to be converted to soluble iron species in the stomach was determined by pH-stat titration at pH 2 and 3, at 37° C. These PH conditions were chosen because the pH of the gastric contents may range from about to about 1 to about 3.5.

Self supporting mounts for X-ray powder diffraction (XRD) were prepared from samples that had been gently ground in an agate mortar. The sample was back-filled into an aluminum sample holder and gently pressed against unglazed paper. Step-scanned XRD patterns were obtained at 0.05° increments and 2 second counting time per increment using CoKα radiation (35 kV and 25 mA) at a Phillips PW 3100 goniometer equipped with a 1° divergence slit, a 0.2 mm receiving slit, and a graphite monochromator.

Results and Discussion

The XRD pattern of the synthesized materials confirms their identity as goethite and ferrihydrite. All of the diffraction lines in the goethite pattern could be attributed to goethite, indicating that no other crystalline phases were present. The diffraction lines were sharp and narrow indicating that the goethite is highly crystalline. The diffraction pattern of ferrihydrite, on the other hand, showed only 2 broad diffraction lines at 2.6 Angstroms and 1.5 Angstroms which are characteristic of 2-line ferrihydrite.

The ratio of oxalate soluble iron to total iron ($Fe_o/Fe_t$) gives additional information on the purity of the two phases. Well-crystallized iron oxide minerals such as goethite are relatively insoluble in oxalate and have $Fe_o/Fe_t$ ratios less than 0.03, while poorly crystallized minerals such as ferrihydrite have $Fe_o/Fe_t$ ratios which approach 1.0. The synthetic goethite had an $Fe_o/Fe_t$ ratio of 0.01 indicating that it contained only goethite, while the synthetic ferrihydrite had an $Fe_o/Fe_t$ ratio of 0.97, indicating that it was essentially pure ferrihydrite.

Surface area data supports both the XRD and oxalate ratio findings. Goethite had a surface area of $82\pm3$ m$^2$/g. This relatively low value is characteristic of its crystalline nature, previously noted by XRD and oxylate ratio evaluations. Ferrihydrite had a surface area of $405\pm22$ m$^2$/g, which is characteristic of a very poorly crystallized solid.

Langmuir absorption isotherms were determined for goethite and ferrihydrite. The adsorption capacities are 6.1 mgP/g for goethite and 53.9 mgP/g for ferrihydrite. The adsorptive co-efficients are 16.2 L/mol for goethite and 15.6 L/mol for ferrihydrite. The adsorptive co-efficients, which are a measure of the strength of binding forces for absorption, are similar. This indicates that the difference between the two compounds is most likely a reflection of the amount of surface available for binding and not a difference in mechanism or strength of binding. The difference in adsorptive capacities can be attributed to the difference in surface area. The higher surface area compound, ferrihydrite, binds more phosphate than goethite.

A study was conducted to compare the amount of phosphorus adsorbed by synthetic goethite and synthetic ferrihydrite at phosphate concentrations similar to that achieved in intestinal fluid following meal. The synthetic ferrihydrite has been found to adsorb 3-5 times more phosphorus per gram than aluminum hydroxide suspensions. One 10 ml dose of Amphogel TM, containing 420 mg equivalent $Al_2O_3$ adsorbs 3.9 mg P. In comparison, 174 mg of synthetic ferrihydrite or 1.05 g of synthetic goethite also adsorbs 3.9 mg P when in equilibrium with a solution containing 0.11 mg P/ml. Thus, a tablet or capsule containing 174 mg synthetic ferrihydrite is predicted to adsorb the same amount of phosphate as 10 ml of Amphogel TM, a product now commercially utilized as a phosphate binder to treat or prevent hyperphosphatemia.

Phosphate absorption occurs in the intestine. However, the minimum gastric residence time in an oral product is estimated to be 15 minutes. The acidity of the gastric contents may vary from pH 1.0 to 3.5. Dissolution of the phosphate binder due to the low pH of the stomach may lead to systemic absorption. Systemic absorption from long term use of aluminum-containing phosphate binders has led to aluminum toxicity resulting in secondary illnesses such as osteomalacic dialysis osteodystrophy, and dialysis dementia. Thus, the rate of acid dissolution under simulated gastric conditions was determined by pH-titration at pH 2 and 3. Table 1 lists the percent dissolved for both aluminum hydroxide and iron oxide compounds during the exposure to simulated gastric conditions.

TABLE 1

| Rate of acid dissolution under simulated gastric conditions. | | | | |
|---|---|---|---|---|
| | Percent Dissolved | | | |
| | pH 2 | | pH 3 | |
| Adsorbent | 15 min | 60 min | 15 min | 60 min |
| Alternagel | | | 22 | 100 |
| Amphogel | | | 68 | 100 |
| Basaljel | | | 74 | 100 |
| Synthetic goethite | 0.3 | 0.6 | 0.3 | 0.6 |
| Synthetic ferrihydrite | 1 | 6 | 0.3 | 4 |

Virtually no dissolution of synthetic goethite or synthetic ferrihydrite occurred, even at pH 2 for 60 minutes. In contrast, the aluminum hydroxide phosphate binders were completely dissolved when exposed to pH 3 for 60 minutes. Oxy-iron compounds, most preferably ferrihydrite and other oxy-iron compounds exhibiting surface areas in excess of 200 m$^2$/g, due to their high phosphate adsorptive capacity and low solubility in gastric fluids, are therapeutic agents of choice for the treatment and prevention of hyperphosphatemia.

What is claimed:

1. Method of controlling serum phosphate level in patients suffering from hyperphosphatemia or patients predisposed to development of a hyperphosphatemic condition, which method comprises contacting ingested phosphate with a oxy-iron compound selected from the group consisting of iron oxides, iron oxyhydroxides and iron hydroxides, in an amount effective to bind sufficient ingested phosphate to prevent or alleviate a condition of hyperphosphatemia.

2. The method of claim 1 wherein the oxy-iron compound has a surface area of at least about 50 m$^2$/g 3. The method of claim 1 wherein the compound has a surface area of at least 200 m$^2$/g.

4. The method of claim 1 wherein the oxy-iron compound is administered to the patient orally for contact with ingested phosphate in the digestive tract.

5. The method of claim 4 wherein the iron-oxy compound has a surface area of about 50 to about 500 m$^2$/g.

6. The method of claim 5 wherein the oxy-iron compound is an iron oxide or iron oxyhydroxide.

7. The method of claim 6 wherein the oxy-iron compound is goethite.

8. The method of claim 6 wherein the oxy-iron compound is ferrihydrite.

9. The method of claim 1 wherein the oxy-iron compound is a component of a dialysate and is contacted with the phosphate during patient hemodialysis.

10. The method of claim 9 wherein the oxy-iron compound is an iron oxide or an iron oxyhydroxide.

11. The method of claim 10 wherein the oxy-iron compound has a surface area of about 50 to about 500 $m^2/g$.

12. The method of claim 10 wherein the oxy-iron compound is goethite.

13. The method of claim 10 wherein the oxy-iron compound is ferrihydrite.

14. A therapeutic composition in oral dosage form for controlling serum phosphate in patients having need for reduced absorption of dietary phosphate, said composition comprising on a per dose basis from about 50 mg. to about 500 mg. of an oxy-iron compound selected from the group consisting of iron oxides, iron oxyhydroxides, and iron hydroxides, and a pharmaceutically acceptable excipient for said oral dosage form.

15. The composition of claim 14 wherein the oxy-iron compound has a surface area of about 50 to about 500 $m^2/g$.

16. The composition of claim 14 wherein the compound is goethite.

17. The composition of claim 14 wherein the iron compound is ferrihydrite.

18. A method for enhancing reduction of a patient's serum phosphate levels during hemodialysis of said patient using a dialysate, said method comprising the step of contacting the dialysate with an oxy-iron compound selected from the group consisting of iron hydroxide, iron oxyhydroxide and iron oxide with the dialysate in an amount sufficient to reduce the concentration of phosphate in said dialysate.

19. The method of claim 18 wherein the oxy-iron compound has a surface area of about 50 to about 500 $m^2/g$.

20. The method of claim 18 wherein the oxy-iron compound is ferrihydrite.

* * * * *